US008361506B2

(12) United States Patent
Ziegler et al.

(10) Patent No.: US 8,361,506 B2
(45) Date of Patent: *Jan. 29, 2013

(54) FAST RELEASE DOSAGE FORMS FOR ANTIBIOTICS

(75) Inventors: Iris Ziegler, Roetgen (DE); Johannes Bartholomäus, Aachen (DE); Jessica Redmer, Mönchengladbach (DE)

(73) Assignee: Gruenenthal GmbH, Aachen (DE)

( * ) Notice: Subject to any disclaimer, the term of this patent is extended or adjusted under 35 U.S.C. 154(b) by 433 days.

This patent is subject to a terminal disclaimer.

(21) Appl. No.: 11/767,228

(22) Filed: Jun. 22, 2007

(65) Prior Publication Data

US 2008/0050446 A1 Feb. 28, 2008

Related U.S. Application Data

(63) Continuation of application No. PCT/EP2005/056795, filed on Dec. 14, 2005.

(30) Foreign Application Priority Data

Dec. 23, 2004 (DE) .......................... 10 2004 063 409
Sep. 8, 2005 (DE) .......................... 10 2005 042 875

(51) Int. Cl.
 *A61K 9/14* (2006.01)
 *A61K 33/42* (2006.01)
(52) U.S. Cl. ......................................... 424/489; 424/602
(58) Field of Classification Search .................. 424/489, 424/602
See application file for complete search history.

(56) References Cited

U.S. PATENT DOCUMENTS

| 5,292,461 | A | * | 3/1994 | Juch et al. ................... 264/37.29 |
| 5,350,584 | A |   | 9/1994 | McClelland et al. |
| 5,356,625 | A | * | 10/1994 | Ying ............................. 424/94.1 |
| 5,705,190 | A | * | 1/1998 | Broad et al. ................... 424/465 |
| 6,159,504 | A |   | 12/2000 | Kumabe |
| 6,531,152 | B1 |  | 3/2003 | Lerner et al. |
| 2003/0039956 | A1 | | 2/2003 | Choi et al. |
| 2003/0064097 | A1 | | 4/2003 | Patel et al. |
| 2003/0072798 | A1 | * | 4/2003 | Schwarz ....................... 424/456 |
| 2003/0104063 | A1 | | 6/2003 | Babcock et al. |

FOREIGN PATENT DOCUMENTS

| EP | 0 276 781 A2 | 8/1988 |
| WO | WO 2004/000202 A1 | 12/2003 |
| WO | WO 2004/000264 A1 | 12/2003 |

OTHER PUBLICATIONS

German Search Report dated Nov. 15, 2006 with English Translation (Nine (9) pages).
International Search Report dated May 4, 2006 with an English translation of the pertinent portions (Seven (7) pages).
Form PCT/ISA/220 dated May 4, 2006 and Form PCT/ISA/237 including an English translation of the pertinent portions (Thirteen (13) pages).
Waiver of In Vivo Bioavailability and Bioequivalence Studies for Immediate-Release Solid Oral Dosage Forms Based on a Biopharmaceutics Classification System, Guidance for Industry, U.S. Department of Health and Human Services, Food and Drug Administration, and Center for Drug Evaluation and Research (CDER), Aug. 2000.

\* cited by examiner

*Primary Examiner* — Paul Zarek

(74) *Attorney, Agent, or Firm* — Crowell & Moring LLP

(57) ABSTRACT

A multiparticulate, pharmaceutical dosage form containing at least one antibiotic which is sparingly wettable with aqueous media or sparingly soluble in aqueous media and a combination of carrageenan and tricalcium phosphate and optionally sucrose ester. Also, an administration system having this dosage form arranged in a drinking straw with at least one barrier device for single administration, optionally together with a conveying liquid.

25 Claims, No Drawings

FAST RELEASE DOSAGE FORMS FOR ANTIBIOTICS

CROSS-REFERENCE TO RELATED APPLICATIONS

This application is a continuation of International patent application Serial No. PCT/EP2005/056795 filed Dec. 14, 2005, which claims benefit to German patent application Serial No. 10 2004 063 409.2 filed Dec. 23, 2004 and German patent application Serial No. 10 2005 042 875.4 filed Sep. 8, 2005, the entire disclosures of which are hereby incorporated in their entirety.

FIELD OF THE INVENTION

The claimed invention relates to a multiparticulate, pharmaceutical dosage form, preferably in the form of extruded pellets containing at least one antibiotic which is sparingly wettable with aqueous media and/or sparingly soluble in aqueous media and a combination of carrageenan and tricalcium phosphate and optionally at least one sucrose ester and to an administration system comprising this dosage form arranged in a drinking straw, preferably for single administration.

BACKGROUND OF THE INVENTION

Antibiotics against most pathogenic bacteria have been developed, but problems may often occur during the use thereof.

Many antibiotics, for instance, exhibit a low solubility in an aqueous medium, i.e. at their strongest dose they are only poorly or not at all soluble at 37° C. in aqueous media with a pH of 1 to 7.5, in particular in corresponding standard buffer solutions of $\leq 250$ ml. It is here particularly unfavourable if this low solubility occurs at pH values which correspond to the physiological pH values in the environment of the small intestine. The antibiotic should in fact be available as fast as possible in the small intestine, since it is there that absorption of the antibiotic mainly takes place. Many antibiotics are therefore preferably administered as a solution or suspension in order to achieve the highest possible bioavailability.

Furthermore, numerous antibiotics often also have a particularly bitter flavor which means that, despite being flavored, such solutions or suspensions are taken only unwillingly by patients, in particular by children.

As a consequence, during treatment with antibiotics, which usually lasts for several days, it becomes ever more difficult to motivate the patient to complete the course of treatment. The unwillingness of patients to take the medicine thus often results in premature termination of treatment, which may have particularly harmful effects with antibiotics, such as development of resistance.

Another disadvantage of these administration forms is that the antibiotics are conventionally marketed as powders for suspension in order to facilitate production, transport and storage in comparison to finished solutions or suspensions. The dry substance is converted into a suspension just before it is first administered. However, the prepared suspension must often be kept in the refrigerator and, as explained above, taken over a period of several days.

This means further unpleasantness for the patient since the prepared suspension may undergo a progressive deterioration in flavor over the course of storage or the suspended fractions may agglomerate when left to stand for an extended period, so entailing redispersion and thus impairing dose accuracy.

Moreover, cooling of the suspension, which is often necessary, also impairs unproblematic taking of the antibiotic.

In order to avoid these disadvantages, effervescent tablets may also be used to prepare a suspension, one tablet conventionally corresponding to an individual dose. Such freshly prepared solutions or suspensions nevertheless have a bitter flavor for the patient.

Taking dry antibiotics in the form of granules, pellets or microtablets, packaged in sachets, which must conventionally be swallowed with the assistance of a liquid is also problematic. Children in particular have problems with taking such dosage forms. With dosage forms which have not been flavor-neutralised, it may happen that just some of the antibiotic is released in the mouth within a short time and causes an unpleasant flavor.

When taking dry preparations in this manner, it is also not ensured that the entire necessary dose is swallowed or so quickly swallowed that any only temporary flavor-masking effect is sufficiently effective.

In order to avoid such problems, dosage forms have been developed in which the antibiotic is arranged in a drinking straw preferably in multiparticulate form, from which it is taken by the patient with the assistance of a conveying liquid. With this type of taking, it is particularly advantageous for the multiparticulate dosage form to assume the form of rounded, spherical pellets with a particle size of no more than 800 µm, because such particles are effortlessly conveyed by the patient's sucking up the conveying liquid and may thus be taken in their entirety.

Care must, however, be taken to ensure, preferably taking account of swallowing behaviour of children, that the volume and mass of the particles is kept as small as possible, which entails an elevated active ingredient loading of the multiparticulate dosage forms. As is known, an elevated active ingredient loading is in particular achieved with extruded pellets, which moreover enable the desired smooth, preferably spherical shape. One disadvantage of this type of dosage form, however, is that, due to the auxiliary substances necessarily used in the conventional manufacturing method, the dosage forms usually have a very compact structure and therefore do not disintegrate in water or an aqueous medium or at most do so very slowly or only in part. As is known, this may result in delayed release of the active ingredient, in particular in the case of an antibiotic which is sparingly wettable with aqueous media and/or sparingly soluble in aqueous media. This applies particularly if said sparing wettability or sparing solubility occurs at the physiological pH values in the environment of the upper small intestine, as described above. As a consequence, release of the antibiotic may then not occur to a considerable extent until in the lower part of the intestine.

However, with many antibiotics, this prevents adequate bioavailability, as these are mainly absorbed in the upper portion of the small intestine. This low dissolution rate of the dosage form and thus the delayed release of the active ingredient is in particular observed when using known spheronising agents, such as microcrystalline cellulose, low-substituted hydroxypropylcellulose, hydroxypropylmethylcellulose, which, while indeed giving rise to pellets in the desired, namely spherical, shape and with a smooth surface and to a narrower particle size distribution, bring about delayed, diffusion-controlled release of the active ingredient, especially if the antibiotic is sparingly soluble in aqueous media and/or sparingly wettable.

This is also observed to a still greater extent with the extruded pellets produced with the assistance of the stated spheronising agents after dissolution of a coating which is present and may preferably be resistant to saliva and/or gastric juice and preferably performs a flavor-neutralisation function. Even after pH-dependent dissolution of the coating, despite preswelling or the addition of disintegrants, the pellets disintegrate very slowly or not at all, so delaying release of the antibiotic and limiting bioavailability.

SUMMARY OF THE INVENTION

One object of the present invention is to provide a solid, multiparticulate dosage form of an antibiotic which is sparingly wettable with aqueous media and/or sparingly soluble in aqueous media, which dosage form, in particular in an aqueous medium with a pH value corresponding to the physiological pH values of the small intestine, exhibits a rapid dissolution rate and thus gives rise to rapid bioavailability of the antibiotic in the absorption window, as it is known.

Said object is achieved by the provision of the multiparticulate pharmaceutical dosage form the according to the invention, preferably in the form of extruded pellets, containing at least one antibiotic which is sparingly wettable with aqueous media and/or sparingly soluble in aqueous media and a combination of carrageenan and tricalcium phosphate and optionally at least one sucrose ester, wherein the dosage form releases at least 85% of the antibiotic within 30 minutes at a pH value of 6-7.

This rapid dissolution rate and thus virtually undelayed release of the active ingredient is determined in accordance with the method described hereinafter which is published in "Guidance for Industry, Waiver of In Vivo Bioavailability and Bioequivalence Studies for Immediate-Release Solid Oral Dosage Forms based on a Biopharmaceutics Classification System, pages 1-3/7, published by U.S. Department of Health and Human Services, Food and Drug Administration, Center for Drug Evaluation and Research (CDER), August 2000, BP".

This elevated dissolution rate is in particular not achieved if the known extruded pellets produced using microcrystalline cellulose are provided with a gastric juice-resistant and/or flavor-neutral finish, since, once the film coating has dissolved, further delayed disintegration of such dosage forms is observed, as a result of which release in the small intestine is further delayed in comparison with corresponding uncoated pellets and the bioavailability thereof is consequently impaired.

It is therefore all the more surprising that the dosage forms according to the invention, even if they are provided with a gastric juice-resistant coating, for example for flavor neutralisation, exhibit rapid dissolution at a physiological pH value of 6-7 of the small intestine once such a coating has dissolved and thus give rise within 30 min to the release of at least 85% of an antibiotic which is sparingly wettable with aqueous media and/or sparingly soluble in aqueous media.

The dosage forms provided according to the invention with a finish may therefore in particular be produced as extrudates which can be converted into rounded pellets by spheronisation. Therefore, thanks to the possible elevated active ingredient loading, the reduced requirement for flavor neutralisation in comparison with suspensions, and the rapid dissolution rate at a pH value of 6-7 once any coatings have dissolved, multiparticulate dosage forms obtained by extrusion which contain carrageenan and tricalcium phosphate are particularly suitable as dosage forms according to the invention.

The dosage forms according to the invention preferably contain 5 to 30 wt. %, relative to the total weight of the dosage form, of carrageenan, preferably of kappa-carrageenan.

The weight ratio of tricalcium phosphate to carrageenan in the dosage forms according to the invention preferably amounts to 1:1 to 1:10, particularly preferably to 1:2 to 1:6.

The dosage forms of the composition according to the invention are preferably suitable for antibiotics which are sparingly wettable with aqueous media and/or sparingly soluble in aqueous media, the sparing solubility of which is defined and classified in accordance with the above-mentioned publication "Guidance for Industry". They are preferably suitable for antibiotics from the group comprising penicillins, cephalosporins and macrolides, particularly preferably amoxicillin, clarithromycin, azithromycin (mono- or dihydrate), cefixim, cefpodoxime and/or cefpodoxime proxetil.

In addition to the combination of carrageenan and tricalcium phosphate, the dosage form according to the invention may in addition preferably contain as auxiliaries at least one sucrose ester, preferably with an HLB value of 10-16, particularly preferably of 13-15. The dosage forms according to the invention may furthermore comprise fillers, binders, slip agents, dyes or preservatives as auxiliary substances.

The dosage forms according to the invention, such as extruded pellets, contain no microcrystalline cellulose or other spheronisation auxiliaries such as low-substituted hydroxypropylcellulose, hydroxypropylmethylcellulose, hydroxypropylcellulose, powdered cellulose, sodium carboxymethylcellulose, polyvinylpyrrolidone, provided that they have not yet been provided with a coating, i.e. the stated auxiliary substances are not present in the uncoated particles, such as extruded pellets.

In a preferred embodiment, the dosage forms according to the invention are provided with at least one coating, particularly preferably with a gastric juice-resistant and/or flavor-neutralizing coating, which is in turn preferably applied over a protective coating which isolates the core from the coating.

These coatings are applied in a quantity of 1 to 50 wt. %, relative to the total weight of the dosage forms, depending on nature and function of the coating.

Suitable materials for a gastric juice-resistant coating are preferably methacrylic acid/alkyl(meth)acrylate copolymers, particularly preferably copolymers of methacrylic acid/methyl methacrylate with a ratio of 1:1 to 1:2 such as Eudragit L® or Eudragit S®, very particularly preferably copolymers of methacrylic acid/ethyl acrylate 1:1 such as Eudragit L55®, Eudragit L30D-55®, which dissolve rapidly at a pH value of $\geq 5.5$. Coatings based on celluloses or based on shellac, which are known to a person skilled in the art, may furthermore be applied as gastric juice-resistant coatings. The coatings may be applied with appropriate solutions or dispersions in an organic or aqueous medium, an aqueous medium being preferred. Suitable saliva-resistant coatings are preferably coatings based on Eudragit E or Eudragit EPO.

A person skilled in the art is aware that conventional plasticisers, dyes, slip agents, such as talcum, magnesium stearate and/or glycerol monostearate should or may be added to known coating materials.

According to the invention, "gastric juice" is taken to mean both the natural composition of gastric juice and the artificial preparations similar to gastric juice (pH 1.2-2) which are familiar to a person skilled in the art. Likewise, "release in the small intestine" is taken to mean both release in natural small intestine juice and release in preparations similar to small intestine juice at pH values of 6-7, preferably pH 6.4-6.8, as are defined in relevant pharmacopoeias.

The dosage forms according to the invention are distinguished in that they exhibit an elevated dissolution rate and 85% of the antibiotic is released within 30 min, once an optionally present coating has previously dissolved. This elevated dissolution rate preferably occurs at pH values of 6.4-6.8.

The pH-dependent duration of dissolution of such a coating may be determined by simple preliminary testing in appropriate standard buffer solutions.

The dosage forms according to the invention are produced by the starting materials being mixed, granulated, extruded, subdivided and optionally shaped, preferably spheronised, optionally classified according to size, for instance by sieving, and optionally provided with a saliva- and/or gastric juice-resistant or flavor-neutralizing coating.

Antibiotics, which often exhibit better solubility at low pH values, are preferably protected with gastric juice-resistant coatings, since this provides ideal assistance for flavor masking on taking the dosage form in the drinking straw with preferred beverages, such as for example cola or fruit juices.

A person skilled in the art knows that the components may be added to the mixture simultaneously or in succession. Mixing may likewise proceed in a known mixer or granulator, such that mixing, granulation and extrusion may optionally proceed simultaneously. Granulation may proceed by wet granulation, preferably with water or an aqueous solvent. Suitable solvents are known to a person skilled in the art.

Spheronization, extrusion and coating may in each case proceed in the apparatus known to a person skilled in the art. A fluidized bed apparatus may preferably be used for coating.

In a particularly preferred dosage form according to the invention, the multiparticulate dosage form assumes the form of spherical extruded pellets. According to an administration system comprising a drinking straw with preferably mobile barrier device, as is described in WO 03/079957, WO 2004/000202, WO2004/000264, these may preferably be arranged as a single dose therein and administered to the patient with a conveying liquid.

The descriptions of the administration systems in the stated publications are hereby introduced as a reference and are deemed to be part of the present disclosure.

The present invention also provides an administration system comprising a dosage form according to the invention, preferably as a single dose, arranged in a drinking straw with at least one preferably mobile barrier device for administration to a human patient with the assistance of a conveying liquid.

Suitable conveying liquids are particle-free beverages, preferably aqueous liquids, such as for example water, preferably mineral water, tea, fruit juices, Coca-Cola, carbonated beverages, wherein conveying liquids with an acidic pH value are preferred when using gastric juice-resistant coated, multiparticulate dosage forms, such as for example extruded pellets.

Active ingredient release of the dosage forms according to the invention or the dissolution rate thereof is determined using the method and classification from "Guidance for Industry, Waiver of In Vivo Bioavailability and Bioequivalence Studies for Immediate-Release Solid Oral Dosage Forms based on a Biopharmaceutics Classification System, pages 1-3/7, published by U.S. Department of Health and Human Services, Food and Drug Administration, Center for Drug Evaluation and Research (CDER), August 2000, BP".

A release apparatus with paddle stirrer according to the US Pharmacopeia was used for this purpose and release was measured at a temperature of 37° C. of the release medium and a rotational speed of 100 $min^{-1}$ for the time stated in the Examples and the release medium stated therein. The particular quantity of active ingredient released at any one time was determined by HPLC or UV photometry. According to the classification in the above-stated publication, an immediate-release, solid dosage form is deemed to be a dosage form with an elevated dissolution rate if at least 85% of the active ingredient present in the dosage form is dissolved within 15 to 30 minutes in a predetermined buffer solution with a specific pH value.

EXAMPLES

Uncoated Granules

Example 1

| Per dose | Starting materials |
|---|---|
| 250.0 mg | Clarithromycin Ph. Eur. |
| 100.0 mg | Carrageenan NF (Gelcarin GP-911, kappa-carrageenan) |
| 50 mg | Tricalcium phosphate Ph. Eur. |
| 20.0 mg | Sucrose stearate S-1570, E473 | were produced by mixing the starting materials in a high speed mixer and then wet granulating and extruding the moist granules through an extruder with a 0.5×0.5 mm extrusion die at extrudate temperatures of below 35° C. The extrudates were spheronised in a suitable spheroniser and the resultant pellets were dried in a fluidised bed down to a residual moisture content of below 10%. The dried pellets were classified by the screening method and the 250 to 710 µm fraction of all the screening operations was combined.

Release of these uncoated pellets was firstly determined in 900 ml of phosphate buffer solution (pH 6.4) at 37° C. in accordance with the above-stated method at a rotational speed of 100 $min^{-1}$ for 60 min. The following values show the corresponding release profile of 3 parallel determinations.

| | Release of clarithromycin | | | | |
|---|---|---|---|---|---|
| | Minutes | | | | |
| | 0.0 | 15.0 | 30.0 | 45.0 | 60.0 |
| | Clarithromycin | | | | |
| T1 | 0.0 | 52.4 | 88.7 | 103.2 | 107.8 |
| T2 | 0.0 | 59.0 | 92.7 | 104.7 | 109.2 |
| T3 | 0.0 | 61.2 | 89.5 | 98.7 | 101.7 |

Comparative Example 1

As stated in Example 1, extruded pellets of the following composition were produced:

| Per dose | |
|---|---|
| 250.0 mg | Clarithromycin |
| 62.5 mg | Microcrystalline cellulose (Avicel PH 105) |
| 50.0 mg | Low-substituted hydroxypropylcellulose NF (L-HPC, grade LH 31) |
| 12.5 mg | Sucrose stearate (S-1570, E473) |

Release of the active ingredient from the uncoated pellets was determined in accordance with the above-stated method in 900 ml of buffer solution at pH 6.4 and is listed below:

| | Minutes | | | | | |
|---|---|---|---|---|---|---|
| | 0.0 | 15.0 | 30.0 | 45.0 | 60.0 | 90.0 | 120.0 |

| | Clarithromycin (released) | | | | | |
|---|---|---|---|---|---|---|
| T1 | 0.0 | 26.5 | 27.0 | 33.3 | 39.5 | 48.4 | 54.0 |
| T2 | 0.0 | 31.0 | 28.0 | 34.5 | 40.1 | 48.5 | 56.7 |
| T3 | 0.0 | 20.8 | 28.2 | 34.4 | 40.3 | 48.3 | 56.7 |

The values show that the pellets produced by wet extrusion and spheronisation with microcrystalline cellulose do not disintegrate and do not release the active ingredient sufficiently rapidly.

Comparative Examples 4-11

As stated in Example 1, extruded pellets were produced with 250 mg of clarithromycin and the auxiliary substances stated in Table 1. The release of clarithromycin in 900 ml of buffer solution at pH 6.8 and 150 revolutions per minute in accordance with the above-stated method is likewise stated in Table 1. The values show that neither by using carrageenan NF (Gelcarin GP-911) alone nor by combining it with further spheronisation auxiliaries are pellets obtained which disintegrate sufficient rapidly and release the active ingredient sufficiently rapidly.

Only when the combination of carrageenan and tricalcium phosphate according to the invention is used are pellets obtained with the necessary rapid release for sparingly soluble or sparingly wettable antibiotics.

TABLE 1

Comparative Examples 4-11

| Sucrose ester mg | Weight per dose mg | Spheronisation properties | Carrageenan per dose mg | Further auxiliaries per dose mg | Release of a 250 mg dose in 900 ml pH 6.8, 150 rpm | |
|---|---|---|---|---|---|---|
| | | | | | % released after 15 min | % released after 30 min |
| 20 | 330 | strands, no spheres | 60 | 0 | 59 | 77 |
| 20 | 310 | strands, no spheres | 40 | 0 | 68 | 83 |
| 20 | 420 | good, but pellets predominantly >700 µm | 100 | 50 lactose × H$_2$O | 59 | 82 |
| 20 | 410 | strands, very slow process | 100 | 40 mannitol | 55 | 79 |
| 20 | 380 | good, but pellets predominantly >700 µm | 70 | 40 mannitol | 52 | 69 |
| 20 | 420 | good, but pellets predominantly >700 µm | 100 | 50 mannitol | 60 | 79 |
| 20 | 420 | Tendency to agglomerate | 100 | 50 calcium hydrogenphosphate | 52 | 75 |

Example 2

As stated in Example 1, extruded pellets having the following composition were produced:

| Per dose | Starting materials |
|---|---|
| 447.6 mg | Cefixim x3H$_2$O, appropriately micronised |
| 400.0 mg | Cefixim USP |
| 50.6 mg | Tricalcium phosphate Ph. Eur. |
| 194.8 | Carrageenan NF |

Release of the active ingredient from the uncoated pellets was determined in accordance with the above-stated method in 900 ml of buffer solution at pH 6.8 and is listed below:

| | Minutes | | | | |
|---|---|---|---|---|---|
| | 0.0 | 15.0 | 30.0 | 45.0 | 60.0 |
| | Cefixim | | | | |
| T1 | 0.0 | 86.6 | 94.0 | 94.2 | 94.2 |
| T2 | 0.0 | 86.4 | 93.9 | 93.7 | 93.7 |
| T3 | 0.0 | 87.1 | 93.8 | 94.1 | 94.1 |

Example 3

Coated Granules

Some of the pellets from Example 1 were in each case coated with aqueous dispersions of the following composition:

| Dispersion composition for the particular coatings | | |
|---|---|---|
| Per dose | | |
| 29.4 mg | Hypromellose 3 mPa · s, Ph. Eur. (hydroxypropylmethylcellulose) | Protective coating |
| 8.8 mg | Titanium dioxide, Ph. Eur. | |
| 3.8 mg | Macrogol 6000, Ph. Eur (polyethylene glycol MG 6000) | |
| 15.2 mg | Triethyl citrate, Ph. Eur. | |

-continued

Dispersion composition for the particular coatings

Per dose

| | | |
|---|---|---|
| 3.0 mg | Glycerol monostearate, Ph. Eur. | |
| 120.4 mg as dry substance | Methacrylic acid/ethyl acrylate copolymer 1:1, 30%, aqueous dispersion, Ph. Eur. (Eudragit L30 D-55) | Gastric juice-resistant film coating |
| 0.1 mg | Polysorbate 80, Ph. Eur | |

The pellets were firstly coated with an aqueous dispersion with 11 wt. % solids content and then with an aqueous dispersion with 15 wt. % solids content in a fluidised bed installation at a product temperature of 45° C. up to a weight gain of 10 wt. %, relative to the weight of the pellets, as a protective coating and then, in order to obtain a gastric juice-resistant film coating, coated, with introduction of hot air, at a product temperature of 30° C. up to a weight gain of 30 wt. %, relative to the weight of the pellets and of the protective coating, and, with reduced feed of hot air, dried until a product temperature of 40° C. and a residual moisture content of <10% are obtained.

Release of the active ingredient from the coated pellets was measured in accordance with the above-stated method at a rotational speed of 100 min$^{-1}$, initially for 30 min in 300 ml of buffer solution at pH 2 and then for 60 min in 1000 ml of phosphate buffer solution at pH 6.8.

The following release values were obtained:

Release from coated pellets

| | Minutes | | | | |
|---|---|---|---|---|---|
| | 0.0–30 | 45.0 | 60.0 | 75.0 | 90.0 |
| | Clarithromycin | | | | |
| T1 | 0.0 | 66.4 | 96.9 | 96.4 | 97.2 |
| T2 | 0.0 | 74.5 | 96.9 | 96.5 | 97.5 |
| T3 | 0.0 | 77.2 | 96.1 | 95.8 | 102.0 |
| T4 | 0.0 | 81.3 | 94.8 | 94.3 | 96.4 |
| T5 | 0.0 | 85.6 | 94.2 | 96.2 | 95.2 |
| T6 | 0.0 | 85.4 | 93.4 | 95.4 | 95.3 | pH = 2 for 30 min → pH = 6.8 for 60 min

Comparative Example 2

As stated in Example 1, extruded pellets of the following composition were produced:

| Per dose | |
|---|---|
| 250.0 mg | Clarithromycin |
| 75.0 mg | Microcrystalline cellulose (PH 101, Ph. Eur.) |
| 25.0 mg | Low-substituted hydroxypropylcellulose NF (L-HPC, grade LH 21) |
| 20.0 mg | Polysorbate 80 (Ph. Eur.) |
| 180.0 mg | Lactose monohydrate (grade 230, Ph. Eur.) |
| 550.0 mg | Purified water (Ph. Eur.) |

The resultant extruded pellets were coated with an aqueous dispersion of the following composition:

Composition of the aqueous dispersion for coating

Per dose

| | |
|---|---|
| 69.5 mg | Talcum (Ph. Eur.) |
| 13.2 mg | Triethyl citrate (Ph. Eur.) |
| 66.0 mg as dry substance | Methacrylic acid/ethyl acrylate copolymer 1:1, 30% aqueous dispersion, Ph. Eur. (Eudragit L30 D55) |

Weight gain, relative to the weight of the pellets, due to the coating was 18 wt. %.

Release of the active ingredient from some of the coated pellets was determined in accordance with the above-described method in 900 ml of buffer solution at pH 6.4 and is stated below:

| | Minutes | | | | |
|---|---|---|---|---|---|
| | 0.0 | 15.0 | 30.0 | 45.0 | 60.0 |
| | Clarithromycin | | | | |
| T1 | 0.0 | 44.6 | 71.3 | 84.2 | 92.3 |
| T2 | 0.0 | 50.2 | 75.8 | 89.9 | 97.2 |

Despite the rapid dissolution of the coating at pH 6.4, release from the pellets proceeds only very slowly since there is no observable disintegration of the pellets.

Release of the active ingredient from some of the coated pellets was determined in accordance with the above-stated method, initially in 300 ml at pH 2 for 30 min and then in 100 ml at pH 6.8, and is stated below:

| | Minutes | | | | | | |
|---|---|---|---|---|---|---|---|
| | 30.0 | 45.0 | 60.0 | 75.0 | 90.0 | 120.0 | 180.0 |
| | Clarithromycin pH change | | | | | | |
| T1 | 0.0 | 38.6 | 56.2 | 67.7 | 76.0 | 83.8 | 87.6 |
| T2 | 0.0 | 37.2 | 55.3 | 67.1 | 73.5 | 81.0 | 84.3 |
| | pH = 2 | | | pH = 6.8 | | | |

The pellets swelled in gastric juice, although the coating did not dissolve at pH 2. It was, however, permeable to water. Nevertheless, even after the complete dissolution thereof at pH 6.8, release was distinctly delayed relative to the uncoated pellets and the pellets did not disintegrate.

Example 4

As stated in Example 1, extruded pellets having the following composition were produced:

| Per dose | Starting materials |
|---|---|
| 575.00 mg | Amoxicillin trihydrate Ph. Eur., = 500 mg Amoxicillin, anhydrous |
| 65.00 mg | Tricalcium phosphate, Ph. Eur. |
| 250.00 mg | Carrageenan NF |

Using the combined screening fractions with a particle size of 250 to 710 μm, release of the active ingredient from the uncoated pellets was determined in accordance with the above-stated method in phosphate buffer (pH 6.8) in 900 ml for 30 minutes and is stated in the following Table:

| | Minutes | | | | |
|---|---|---|---|---|---|
| | 0.0 | 1.0 | 5.0 | 10.0 | 15.0 | 30.0 |
| | Amoxicillin | | | | | |
| T1 | 0.0 | 23.9 | 97.8 | 100.7 | 100.6 | 97.5 |
| T2 | 0.0 | 53.9 | 107.1 | 104.8 | 101.7 | 101.0 |
| T3 | 0.0 | 46.6 | 99.4 | 93.6 | 91.2 | 90.0 |

As stated in Example 3, some of the extruded pellets were also coated with an aqueous dispersion of the following composition up to a weight gain of 2 wt. %, relative to the weight the pellets:

| Composition of the aqueous coating dispersions | |
|---|---|
| Per dose | |
| 15.51 mg as dry substance | Methacrylic acid/ethyl acrylate copolymer 1:1, 30% aqueous dispersion, (Eudragit L30 D-55), Ph. Eur. |
| 1.91 mg | Triethyl citrate, Ph. Eur. |
| 0.36 mg | Glycerol monostearate (Cutina V, plant origin), Ph. Eur. |
| 0.02 mg | Polysorbate 80 Ph. Eur. |

Determination of release in accordance with the above-described method at pH 6.8 in 900 ml of buffer solution for 10 minutes revealed the following values:

| | Minutes | | |
|---|---|---|---|
| | 0.0 | 5.0 | 10.0 |
| | Amoxicillin (released) | | |
| T1 | 0.0 | 86.2 | 96.9 |
| T2 | 0.0 | 85.1 | 98.0 |
| T3 | 0.0 | 85.3 | 97.1 |

The release values showed virtually identical release profiles for coated and uncoated amoxicillin pellets. This makes it clear that it is not the coating, which merely serves to provide flavor masking, but instead the composition according to the invention of the dosage form which enables very rapid release in the environment of the small intestine and thus rapid bioavailability.

Comparative Example 3

As stated in Example 1, extruded pellets having the following composition were produced:

| Per dose | Starting materials |
|---|---|
| 581.00 mg | Amoxicillin trihydrate = 500 mg amoxicillin, anhydrous, Ph. Eur. |
| 73.0 mg | Microcrystalline cellulose, grade PH101, Ph. Eur. |
| 73.00 mg | Low-substituted hydroxypropylcellulose, grade LH21, NF |

Release of the active ingredient from these extruded pellets was determined in accordance with the above-stated method in 900 ml of buffer solution at pH 6.8 and is stated below:

| | Minutes | | | | |
|---|---|---|---|---|---|
| | 0.0 | 15.0 | 30.0 | 45.0 | 60.0 |
| | Amoxicillin (released) | | | | |
| T1 | 0.0 | 29.2 | 43.4 | 59.5 | 69.7 |
| T2 | −0.1 | 29.8 | 44.2 | 60.8 | 71.0 |
| T3 | 0.0 | 29.3 | 43.9 | 60.0 | 70.4 |
| T4 | 0.1 | 29.4 | 43.8 | 60.2 | 70.5 |
| T5 | 0.0 | 29.4 | 43.7 | 59.8 | 70.2 |
| T6 | −0.1 | 29.3 | 43.2 | 59.6 | 69.7 |

As stated in Example 3, some of the extruded pellets were also coated with an aqueous dispersion of the following composition up to a weight gain of 2 wt. %, relative to the weight the pellets:

| Composition of the aqueous coating dispersions | |
|---|---|
| Per dose | |
| 15.51 mg as dry substance | Methacrylic acid/ethyl acrylate copolymer 1:1, 30% aqueous dispersion, (Eudragit L30 D-55), Ph. Eur. |
| 1.91 mg | Triethyl citrate, Ph. Eur. |
| 0.36 mg | Glycerol monostearate (Cutina V, plant origin), Ph. Eur. |
| 0.02 mg | Polysorbate 80 Ph. Eur. |

Determination of release in accordance with the above-described method at pH 1.2 in 900 ml of buffer solution for 90 minutes revealed the following values:

| | Minutes | | | | | | |
|---|---|---|---|---|---|---|---|
| | 0.0 | 6.0 | 15.0 | 30.0 | 45.0 | 60.0 | 90.0 |
| | Amoxicillin | | | | | | |
| Mean from n = 3 | 0 | 8 | 20 | 35 | 43 | 50 | 58 |

Example 5

As stated in Example 1, extruded pellets having the following composition were produced:

| Per dose | |
|---|---|
| 20.0 mg | Sucrose stearate S-1570 |
| 250.0 mg = 256 mg | Azithromycin (monohydrate) |
| 50.0 mg | Tricalcium phosphate |
| 100.0 mg | Carrageenan NF |

The combined screening fractions with a particle size of 250 to 710 µm were coated as stated in Example 3 with the coating dispersions described below:

| Composition of the aqueous coating dispersion | |
|---|---|
| Per dose | |
| 29.4 mg | Hypromellose 3 mPa·s, Ph. Eur. } |
| 8.8 mg | Titanium dioxide, Ph. Eur. |

-continued

Composition of the aqueous coating dispersion

Per dose

| | | |
|---|---|---|
| 3.8 mg | Macrogol 6000, Ph. Eur (polyethylene glycol 600) | Protective coating |
| 15.2 mg | Thethyl citrate, Ph. Eur. | |
| 3.0 mg | Glycerol monostearate, Ph. Eur. | |
| 120.4 mg as dry substance | Methacrylic acid/ethyl acrylate copolymer, 1:1, 30% aqueous dispersion, Ph. Eur. (Eudragit L30 D55) | Gastric juice-resistant film coating |
| 0.1 mg | Polysorbate 80, Ph. Eur. | |

Active ingredient release of the coated pellets was measured in 900 ml of phosphate buffer solution (pH 6.4) at 37° C. in accordance with the above-stated method and is listed below:

| | Minutes | | | |
|---|---|---|---|---|
| | 0.0 | 15.0 | 30.0 | 45.0 |
| | | Azithromycin release | | |
| T1 | 0.0 | 96.3 | 96.5 | 95.7 |
| T2 | 0.0 | 95.0 | 94.4 | 93.5 |
| T3 | 0.0 | 94.8 | 94.1 | 93.1 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A multiparticulate, pharmaceutical dosage form comprising at least one antibiotic which is sparingly wettable with aqueous media or is sparingly soluble in aqueous media and a combination of carrageenan and tricalcium phosphate, wherein said dosage form contains 5 to 50 wt. % of carrageenan relative to the total weight of the dosage form and the weight ratio of tricalcium phosphate to carrageenan is from 1:1 to 1:10, and, at a pH value of 6-7, the antibiotic is released in a quantity of at least 88% within 30 min.

2. A dosage form according to claim 1, further comprising at least one sucrose ester.

3. A dosage form according to claim 1, wherein said dosage form is provided in the form of extruded pellets.

4. A dosage form according to claim 3, where said extruded pellets have a spherical form.

5. A dosage form according to claim 2, wherein the sucrose ester exhibits an HLB of 10-16.

6. A dosage form according to claim 2, wherein the sucrose ester exhibits an HLB of 13-15.

7. A dosage form according to claim 1, wherein said dosage form contains preferably 20-30 wt. % of carrageenan relative to the total weight of the dosage form.

8. A dosage form according to claim 1, wherein said carrageenan is kappa-carrageenan.

9. A dosage form according to claim 1, wherein the weight ratio of tricalcium phosphate to carrageenan is from 1:2 to 1:6.

10. A dosage form according to claim 1, wherein the tricalcium phosphate is present as a finely divided powder with a particle size of <50 μm.

11. A dosage form according to claim 2, wherein the sucrose ester is present in a quantity of from 1-10 wt. % relative to the total weight of the dosage form.

12. A dosage form according to claim 2, wherein the sucrose ester is present in a quantity of from 4-6 wt. % relative to the total weight of the dosage form.

13. A dosage form according to claim 1, further comprising at least one antibiotic selected from the group consisting of penicillins, cephalosporins and macrolides.

14. A dosage form according to claim 13, wherein the at least one antibiotic is amoxicillin, clarithromycin, azithromycin (mono- or dihydrate) or cefixim, cefpodoxime or cefpodoxime proxetil.

15. A dosage form according to claim 1, further comprising a gastric juice-resistant or saliva-resistant, flavor-neutral coating.

16. A dosage form according to claim 1, wherein the particles have a size of <800 μm.

17. A dosage form according to claim 1, wherein the dosage form comprises amoxicillin and a flavor-neutralizing coating.

18. A dosage form according to claim 1, wherein the dosage form comprises clarithromycin and a flavor-neutralizing coating.

19. A method for producing a multiparticulate, pharmaceutical dosage form comprising at least one antibiotic which is sparingly wettable with aqueous media or is sparingly soluble in aqueous media and a combination of carrageenan and tricalcium phosphate, wherein said dosage form contains 5 to 50 wt. % of carrageenan relative to the total weight of the dosage form and the weight ratio of tricalcium phosphate to carrageenan is from 1:1 to 1:10, and, at a pH value of 6-7, the antibiotic is released in a quantity of at least 88% within 30 minutes, said method comprising the steps of:
    mixing, granulating, extruding, subdividing and spheronizing the starting materials.

20. A method according to claim 19, further comprising the step of classifying the starting materials by size.

21. A method according to claim 19, further comprising the steps of providing at least one of a saliva-resistant, a gastric juice-resistant and a flavor-neutral coating.

22. A method according to claim 19, further comprising the step of moist granulating the starting materials.

23. An administration system comprising a multiparticulate, pharmaceutical dosage form comprising at least one antibiotic which is sparingly wettable with aqueous media or is sparingly soluble in aqueous media and a combination of carrageenan and tricalcium phosphate, wherein said dosage form contains 5 to 50 wt. % of carrageenan relative to the total weight of the dosage form and the weight ratio of tricalcium phosphate to carrageenan is from 1:1 to 1:10, and, at a pH value of 6-7, the antibiotic is released in a quantity of at least 88% within 30 minutes, wherein said dosage form is arranged in a drinking straw with at least one preferably mobile barrier device for single administration.

24. An administration system according to claim 23, wherein said dosage form is provided in the form of rounded extruded pellets.

25. A kit comprising an administration system according to claim 23 and a physiologically acceptable conveying liquid with a pH of ≦6.

* * * * *